United States Patent
Nguyen et al.

(10) Patent No.: US 12,119,118 B2
(45) Date of Patent: Oct. 15, 2024

(54) COMPUTE SYSTEM WITH HIDRADENITIS SUPPURATIVA SEVERITY DIAGNOSTIC MECHANISM AND METHOD OF OPERATION THEREOF

(71) Applicant: BelleTorus Corporation, Cambridge, MA (US)

(72) Inventors: Tien Dung Nguyen, Toulouse (FR); Thi Thu Hang Nguyen, Toulouse (FR); Leá Mathilde Gazeau, Toulouse (FR); Mariia Lebedeva, Toulouse (FR); Nga Thi Thuy Nguyen, Toulouse (FR); Jonathan Wolfe, Plymouth Meeting, PA (US)

(73) Assignee: BelleTorus Corporation, Cambridge, MA (US)

( * ) Notice: Subject to any disclaimer, the term of this patent is extended or adjusted under 35 U.S.C. 154(b) by 0 days.

(21) Appl. No.: 18/535,627

(22) Filed: Dec. 11, 2023

(65) Prior Publication Data
US 2024/0194352 A1 Jun. 13, 2024

Related U.S. Application Data

(60) Provisional application No. 63/431,589, filed on Dec. 9, 2022.

(51) Int. Cl.
| | | |
|---|---|---|
| G06T 7/00 | (2017.01) | |
| G06T 7/11 | (2017.01) | |
| G16H 30/40 | (2018.01) | |
| G16H 50/30 | (2018.01) | |

(52) U.S. Cl.
CPC .......... *G16H 50/30* (2018.01); *G06T 7/0012* (2013.01); *G06T 7/11* (2017.01); *G16H 30/40* (2018.01); *G06T 2207/30088* (2013.01)

(58) Field of Classification Search
CPC ...... G16H 50/30; G16H 30/40; G06T 7/0012; G06T 7/11; G06T 2207/30088
See application file for complete search history.

(56) References Cited

U.S. PATENT DOCUMENTS

| | | | |
|---|---|---|---|
| 10,398,641 B2 | 9/2019 | Tamarkin et al. | |
| 11,660,276 B2 | 5/2023 | Bannister et al. | |
| 2003/0053689 A1* | 3/2003 | Watanabe | H04N 1/6027 382/167 |
| 2015/0206022 A1* | 7/2015 | Radha Krishna Rao | G06V 10/42 382/128 |
| 2016/0157786 A1* | 6/2016 | Gupta | A61B 5/7264 600/306 |
| 2018/0064638 A1 | 3/2018 | Tamarkin et al. | |

(Continued)

FOREIGN PATENT DOCUMENTS

WO WO-2023052222 A2 * 4/2023

*Primary Examiner* — Van D Huynh
(74) *Attorney, Agent, or Firm* — Perspectives Law Group, Corp.

(57) ABSTRACT

A method of operation of a compute system includes: verifying a patient image as an acceptable image; detecting a body part from the acceptable image; generating a skin segmentation for the body part including a non-skin region and a skin region based on the acceptable image; and generating a local Hidradenitis Suppurativa (HS) severity score based on the patient image for displaying on a device to assist in diagnosis.

20 Claims, 8 Drawing Sheets
(6 of 8 Drawing Sheet(s) Filed in Color)

(56) References Cited

U.S. PATENT DOCUMENTS

| | | |
|---|---|---|
| 2021/0077441 A1 | 3/2021 | Bannister et al. |
| 2021/0196186 A1* | 7/2021 | Yeates .................. A61B 5/7485 |
| 2021/0275085 A1* | 9/2021 | George ................. G06T 7/0012 |
| 2023/0060162 A1* | 3/2023 | Chen .......................... G06T 7/11 |
| 2023/0235042 A1* | 7/2023 | Zhuang ................... A61P 17/00 |
| | | 424/142.1 |
| 2023/0351587 A1* | 11/2023 | Johannesson .......... G06V 10/42 |
| 2023/0363697 A1* | 11/2023 | Patwardhan ........... A61B 5/445 |

* cited by examiner

COMPUTE SYSTEM WITH HIDRADENITIS SUPPURATIVA SEVERITY DIAGNOSTIC MECHANISM AND METHOD OF OPERATION THEREOF

CROSS REFERENCE TO RELATED APPLICATION(S)

This application claims priority from U.S. Provisional Patent Application Ser. No. 63/431,589 filed Dec. 9, 2022, and the subject matter thereof is incorporated herein by reference thereto.

TECHNICAL FIELD

An embodiment of the present invention relates generally to a compute system, and more particularly to a system with a Hidradenitis Suppurativa severity scoring mechanism.

BACKGROUND

Hidradenitis Suppurativa (HS) is a chronic inflammatory skin disease that has a prevalence vary between 0.03% and 4% of the population. It is a debilitating disease that can cause pain, depression, and poor quality of life, even more than other diseases such as psoriasis and eczema.

Thus, a need still remains for a compute system with a Hidradenitis Suppurativa severity diagnostic mechanism to provide a comprehensive Hidradenitis Suppurativa score to provide for a reproducible score to assist healthcare professionals and payers in the diagnosis of Hidradenitis Suppurativa. In view of the ever-increasing commercial competitive pressures, along with growing healthcare needs, healthcare expectations, and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

An embodiment of the present invention provides a method of operation of a compute system including: verifying a patient image as an acceptable image; detecting a body part from the acceptable image; generating a skin segmentation for the body part including a non-skin region and a skin region based on the acceptable image; and generating a local Hidradenitis Suppurativa (HS) severity score based on the patient image for displaying on a device to assist in diagnosis.

An embodiment of the present invention provides a compute system, including a control circuit, including a processor, configured to a control circuit, including a processor, configured to: verify a patient image as an acceptable image, detect a body part from the acceptable image, generate a skin segmentation for the body part including a non-skin region and a skin region based on the acceptable image, and generate a local Hidradenitis Suppurativa (HS) severity score based on the patient image for displaying on a device to assist in diagnosis.

An embodiment of the present invention provides a non-transitory computer readable medium including instructions for a compute system, including: verifying a patient image as an acceptable image; detecting a body part from the acceptable image; generating a skin segmentation for the body part including a non-skin region and a skin region based on the acceptable image; and generating a local Hidradenitis Suppurativa (HS) severity score based on the patient image for displaying on a device to assist in diagnosis.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
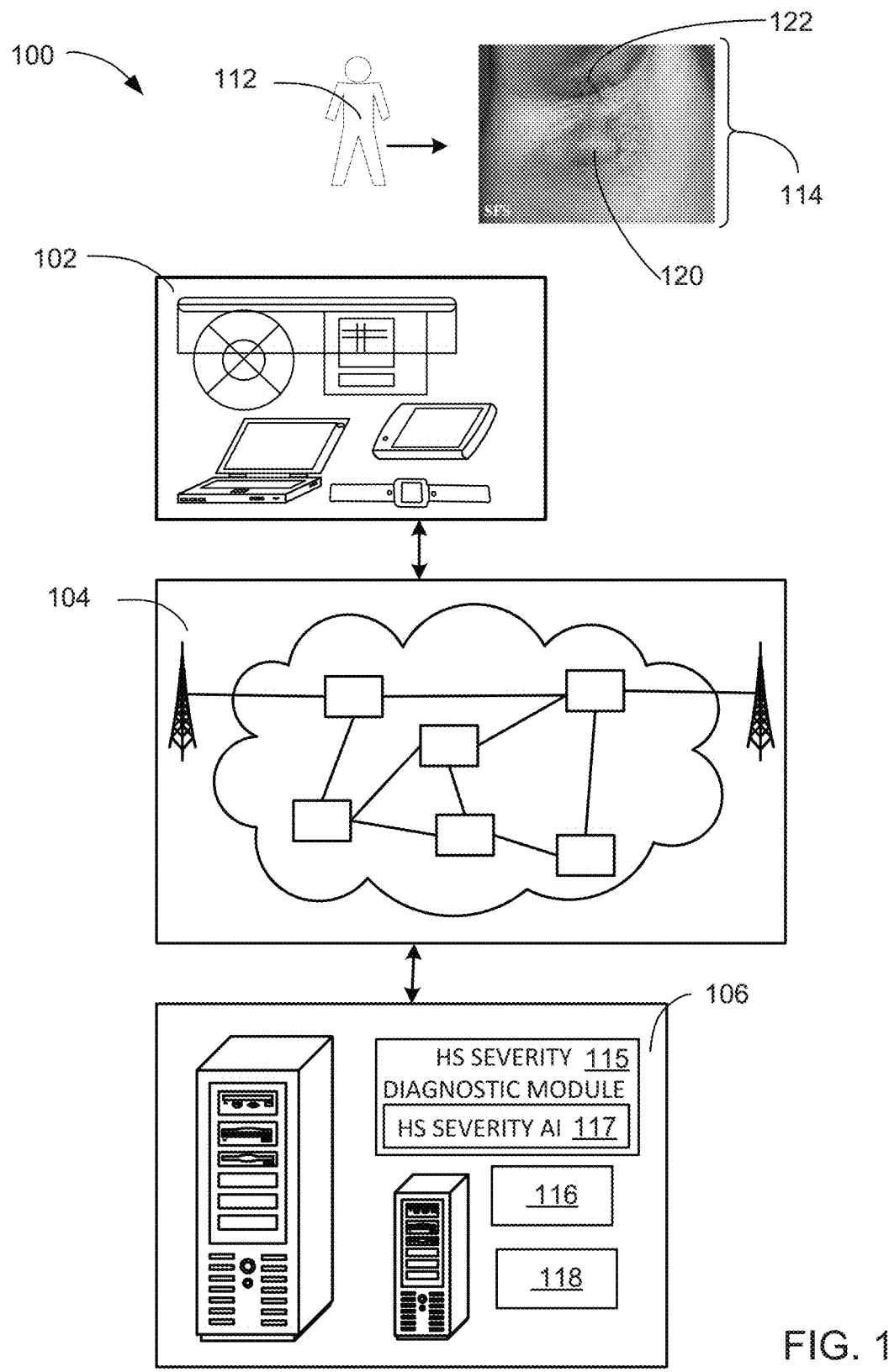
FIG. 1 is an example of a system architecture diagram of a compute system with a Hidradenitis Suppurativa (HS) diagnostic mechanism in an embodiment of the present invention.

The severity assessment of Hidradenitis Suppurativa (hereinafter referred to as "HS") for diagnosis is a challenging problem for dermatologists and clinicians. Scoring methods attempted to deal with this problem. One example of current HS severity evaluation is the Hurley stage (3 stages: 1=mild, 2=moderate, 3=severe), whose main purpose is the choice of treatment, and which is not granular enough for monitoring the evolution of the disease. Other examples of HS severity scoring methods, more granular than Hurley Stage, include Sartorius score, HS-PGA, and Hidradenitis Suppurativa Severity Score System (IHS4). A further example is method called Hidradenitis Suppurativa Clinical Response (HiSCR) can be used for the evaluation of biological treatment performance of HS; this method compares the severity indicators (such as the numbers of subtypes of HS lesions) before and after a treatment.

The examples above and other HS scoring methods do not take into account the surface area of HS lesions or the local severity of each individual HS lesion. For example, for them, a very big nodule/abscess will have the same score as a very small nodule/abscess, even though one big nodule may be more debilitating than three small nodules.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments of various components as a matter of descriptive convenience and are not intended to have any other significance or provide limitations for an embodiment of the present invention.

One skilled in the art would appreciate that the format with which navigation information is expressed is not critical to some embodiments of the invention. For example, in some embodiments, location information is presented in the format of (X, Y, Z); where X and Y and Z are three coordinates, such as latitude, longitude, and elevation that define the geographic location, i.e., a position of a device capturing images.

The term "module" or "unit" or "circuit" referred to herein can include or be implemented as or include software running on specialized hardware, hardware, or a combination thereof in the present invention in accordance with the context in which the term is used. For example, the software can be machine code, firmware, embedded code, and application software. The software can also include a function, a call to a function, a code block, or a combination thereof.

Also, for example, the hardware can be gates, circuitry, processor, computer, integrated circuit, integrated circuit cores, memory devices, a pressure sensor, an inertial sensor, a microelectromechanical system (MEMS), passive devices, physical non-transitory memory medium including instructions for performing the software function, a portion therein, or a combination thereof to control one or more of the hardware units or circuits. Further, if a "module" or "unit" or a "circuit" is written in the claims section below, the "unit" or the "circuit" is deemed to include hardware circuitry for the purposes and the scope of the claims.

The module, units, or circuits in the following description of the embodiments can be coupled or attached to one another as described or as shown. The coupling or attachment can be direct or indirect without or with intervening items between coupled or attached modules or units or circuits. The coupling or attachment can be by physical contact or by communication between modules or units or circuits, such as wireless communication.

It is also understood that the nouns or elements in the embodiments can be described as a singular instance. It is understood that the usage of singular is not limited to singular but the singular usage can be applicable to multiple instances for any particular noun or element in the application. The numerous instances can be the same or similar or can be different.

Referring now to FIG. 1, therein is shown an example of a system architecture diagram of a compute system 100 with a Hidradenitis Suppurativa severity diagnostic mechanism in an embodiment of the present invention. Embodiments of the compute system 100 provide standardized and objective HS severity scoring to provide for a reproducible precise HS severity calculation, especially since healthcare payers rely on Hidradenitis Suppurativa severity calculations to reach payment reimbursement decisions and to enable patients to have access proper treatments.

The compute system 100 can include a first device 102, such as a client or a server, connected to a second device 106, such as a client or server. The first device 102 can communicate with the second device 106 through a network 104, such as a wireless or wired network.

For example, the first device 102 can be of any of a variety of computing devices, such as a smart phone, a tablet, a cellular phone, personal digital assistant, a notebook computer, a wearable device, internet of things (IoT) device, or other multi-functional device that include a display. Also, for example, the first device 102 can be included in a device or a sub-system.

The first device 102 can couple, either directly or indirectly, to the network 104 to communicate with the second device 106 or can be a stand-alone device. The first device 102 can further be separate form or incorporated with a vehicle, such as a car, truck, bus, motorcycle, or a drone.

For illustrative purposes, the compute system 100 is described with the first device 102 as a mobile device, although it is understood that the first device 102 can be different types of devices. For example, the first device 102 can also be a non-mobile computing device, such as a server, a server farm, cloud computing, or a desktop computer.

The second device 106 can be any of a variety of centralized or decentralized computing devices. For example, the second device 106 can be a computer, grid computing resources, a virtualized computer resource, cloud computing resource, routers, switches, peer-to-peer distributed computing devices, or a combination thereof.

The second device 106 can be centralized in a single room, distributed across different rooms, distributed across different geographical locations, embedded within a telecommunications network. The second device 106 can couple with the network 104 to communicate with the first device 102. The second device 106 can also be a client type device as described for the first device 102.

For illustrative purposes, the compute system 100 is described with the second device 106 as a non-mobile computing device, although it is understood that the second device 106 can be different types of computing devices. For example, the second device 106 can also be a mobile computing device, such as notebook computer, another client device, a wearable device, or a different type of client device.

Also, for illustrative purposes, the compute system 100 is described with the second device 106 as a computing device, although it is understood that the second device 106 can be different types of devices. Also, for illustrative purposes, the compute system 100 is shown with the second device 106 and the first device 102 as endpoints of the network 104, although it is understood that the compute system 100 can include a different partition between the first device 102, the second device 106, and the network 104. For example, the first device 102, the second device 106, or a combination thereof can also function as part of the network 104.

The network 104 can span and represent a variety of networks. For example, the network 104 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path. Ethernet, digital subscriber line (DSL), fiber to the home (FTTH), and plain old telephone service (POTS) are examples of wired communication that can be included in the network 104. Further, the network 104 can traverse a number of network topologies and distances. For example, the network 104 can include direct connection, personal area network (PAN), local area network (LAN), metropolitan area network (MAN), wide area network (WAN), or a combination thereof.

Returning to the description standardized and objective HS severity scoring of the embodiments of the compute system 100, as an example, the compute system 100 provide functions to various users 112, including patients and clinicians. The compute system 100 can provide functions to the users 112 in a number of ways.

For example, the compute system 100 can provide the functions for the users 112 with the first device 102, the second device 106, distributed between these two devices, or a combination thereof. Also as examples, the compute system 100 can provide a mobile applications for the patients, the clinicians, or a combination thereof. Further as an example, the compute system 100 can provide the functions via a web-browser based applications or a software to be executed on the first device 102, the second device 106, distributed between these two devices, or a combination thereof.

In one embodiment as an example, patient images 114 are taken and uploaded by the patient, clinician, an assistance, or someone related to providing service to the patient and reviewed by the clinician. In this embodiment as an example, a patient launches the Hidradenitis Suppurativa severity diagnostic mechanism via the mobile application and logs into the patient's account. The patient can be prompted to upload or take body images as the patient images 114. The compute system 100 can guide a patient on photo guidelines for the patient images 114 and accepts or rejects the patient images 114 for retake based on a pre-specified criteria, e.g., distance, quality, blur, or a combination thereof. The compute system 100 can also provide guides for a patient on capturing videos as opposed to still photos. The patient images 114 can be selected from the video or can be submitted as individual photographs.

As an example, the patient image 114 depicted in FIG. 1 is an example where there are 2 lesions, one of them is quite more severe than the other one, though they would have the same scores under the current systems. This example shown as the patient images 114 is an example of HS disease. Two abscesses with different sizes could be clearly seen in the patient image 114. A primary HS lesion 120, which is larger than secondary HS lesions 122 can be differentiated and individually scored by a Hidradenitis Suppurativa (HS) severity diagnostic module 115.

Once the patient images 114, as required for analysis, are successfully uploaded, the compute system 100 can send or load the patient images 114 to the Hidradenitis Suppurativa severity diagnostic module 115 for analysis. The Hidradenitis Suppurativa severity diagnostic module 115 will be described later. For brevity and clarity and as an example, the Hidradenitis Suppurativa severity diagnostic module 115 is shown in FIG. 1 as being executed in the second device 106 although it is understood that portions can operate on the first device 102, such as the mobile app or the web-browser based application, can operate completely on the first device 102, or a combination thereof.

As a further example, the Hidradenitis Suppurativa severity diagnostic module 115 can be implemented in software running on specialized hardware, full hardware, or a combination thereof. The Hidradenitis Suppurativa severity diagnostic module 115 can include a HS severity artificial intelligence (AI) 117. By way of an example, the HS severity AI 117 can include a convolutional neural network and supporting software that is trained to process the patient images 114 to detect a local HS severity score 116 for the primary HS lesion 120 and the secondary HS lesions 122.

Based on analysis results, the compute system 100 can display information to the patient including a recommendation based on the patient images 114, uploaded, for the patient to schedule a visit with your primary care physician or with a specialist based on the local HS severity score 116, which may or may not be visible or displayed to the patient.

If the Hidradenitis Suppurativa severity diagnostic module 115 provides the Local HS severity score 116 aggregated to a full body HS severity score 118, the compute system 100 can display a message that based on the patient images 114, uploaded, the patient may not need a visit with your primary care physician or with another specialist. The compute system 100 can provide a function allowing the patient to schedule a visit with the clinician.

The existing methods have challenges of insufficient granularity (not taking into account the size and the local severity of lesions) and leading to increased likelihood in inconsistency of scoring systems in many situations, e.g. a moderate case may have a higher score than a severe case. In practice, dermatologists sometimes do not follow the scoring formulas in a very strict way, instead they modify the scores in a flexible way by taking into account things (e.g. the surface area) that are not present in the formulas and resulting in more inconsistencies and less objectivity.

The Sartorius scoring system does not consider the extensivity of HS with regards to surface area and local severity as in an embodiment of the present invention. Instead, the Sartorius scoring system utilizes indirect indicators: the "diameter" (how far are the lesions from each other) and the "separability" (if the lesions cannot be separated by normal skin it implies that they are big and dense).

Estimating the surface area and the local severity HS lesions is a very challenging and time consuming task for the clinicians, and that is probably the main reason why the current HS scoring systems in use do not use these indicators directly. However, an embodiment of the present invention can change drastically with the artificial intelligence architecture and models by: calculating the surface area and the local severity of each individual HS lesion, and combining these numbers, of the HS lesions, together by a process to get a more precise, granular and consistent scoring of HS severity.

Continuing the example, the compute system 100 can provide a function that allow the clinician to access the patient images 114 uploaded by the patient and the Local HS severity score 116, such as with the web-based dashboard from the Hidradenitis Suppurativa diagnostic mechanism. The compute system 100 allows the clinician to make edits to annotations determined by the Hidradenitis Suppurativa severity diagnostic module 115 and the scores (if necessary) and saves the results. The clinician can utilize the Local HS severity score 116 to make the diagnostic decision and takes necessary treatment steps (if applicable).

In a further embodiment as an example, the compute system 100 can allow a patient to schedule a visit with a primary care physician or with a specialist. A clinician can launch the Hidradenitis Suppurativa severity diagnostic mechanism, such as a mobile application and logs in. The compute system 100 can be prompted to upload or take the patient images 114 of the patient's body or body parts to be analyzed by the Hidradenitis Suppurativa severity diagnostic module 115.

The compute system 100 can provide guidance to the clinician based on the patient images 114. The compute system 100 can accept or reject the patient images 114 for retake based on a pre-specified criteria, such as distance, quality, blur, or a combination thereof. Once the patient images 114 are successfully uploaded, the compute system 100 and send or load the patient images 114 to the Hidradenitis Suppurativa severity diagnostic module 115 for analysis.

Continuing the example, the compute system 100 can similarly provide a function that allow the clinician to access the patient images 114 uploaded by the patient and the Local HS severity score 116, such as with the web-based dashboard from the Hidradenitis Suppurativa severity diagnostic mechanism. The compute system 100 allows the clinician to make edits to annotations determined by the Hidradenitis Suppurativa severity diagnostic module 115 and the local HS severity score 116 and the full body HS severity scores 118 (if necessary) and saves the results. The clinician can utilize the Local HS severity score 116 to make the diagnostic decision and takes necessary treatment steps (if applicable).

Figure 2:
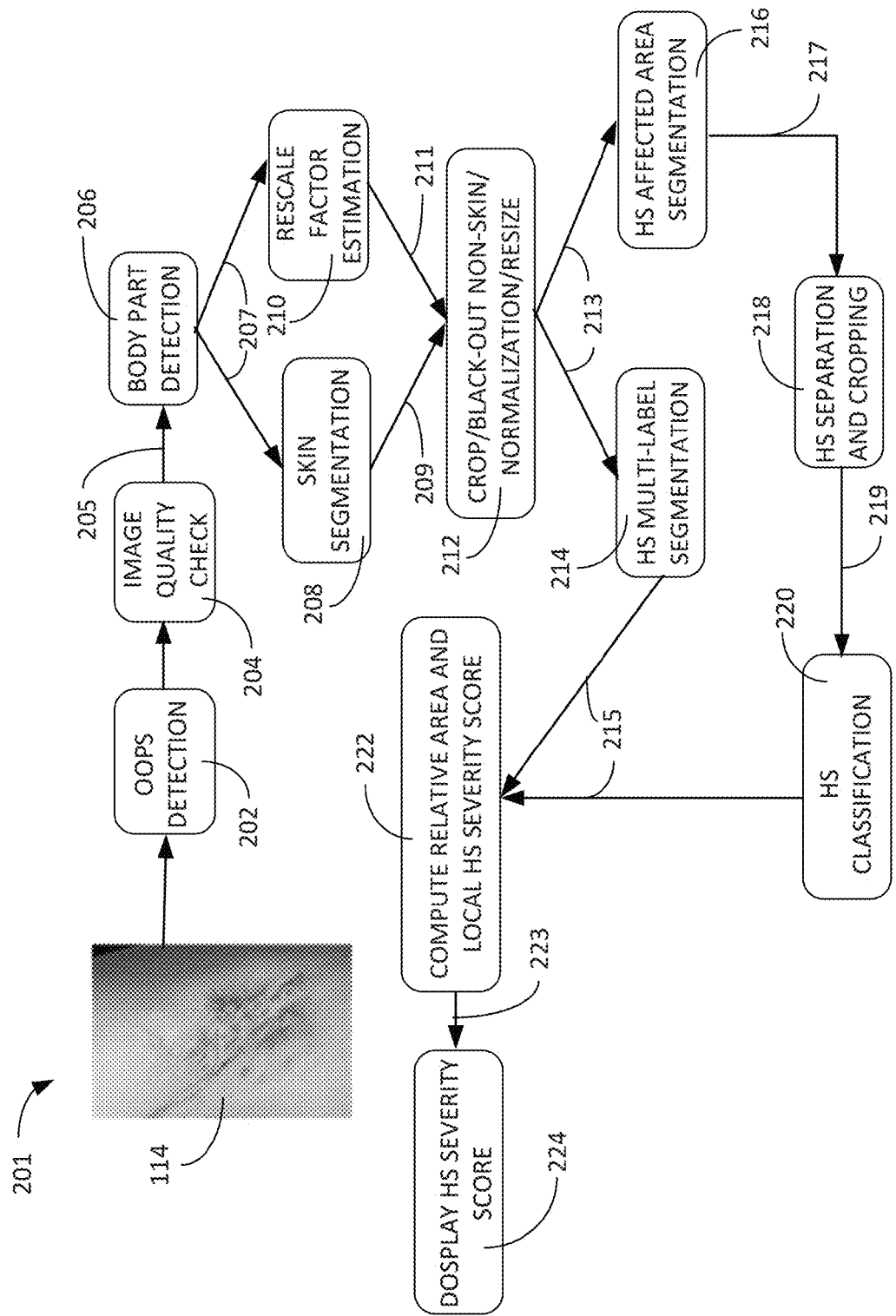
FIG. 2 is an example of a control flow of the compute system with the Hidradenitis Suppurativa (HS) severity diagnostic mechanism in an embodiment.

Referring now to FIG. 2, therein is shown an example of a control flow of the compute system 100 of FIG. 1 with the Hidradenitis Suppurativa diagnostic mechanism in an embodiment. As a specific example, FIG. 2 can depict a flow of the Hidradenitis Suppurativa severity diagnostic module 115 of FIG. 1. The Hidradenitis Suppurativa severity diagnostic module 115 computes the Local HS severity score 116 based on the patient images 114 uploaded for a patient.

The compute system 100 process the patient images 114, each of which can covers a specific part of the body (e.g. the back, the shin, etc.), multiple body parts, different angles of one or more of the body parts, or a combination thereof so that the patient images 114 can cover the full body of a patient or portions of the full body of the patient to be analyzed. The compute system 100, the Hidradenitis Suppurativa severity diagnostic module 115, or a combination thereof can compute the Local HS severity score 116 and aggregate the full body HS severity score 118.

The compute system 100, the Hidradenitis Suppurativa severity diagnostic module 115, or a combination thereof can provide the Local HS severity score 116 for the patient based in the patient images 114 loaded for that patient and for that set of the patient images 114. Continuing with the embodiment as an example to estimate the surface area and the local HS severity score 116 of the primary lesion 120 and any of the secondary lesions 122. The Hidradenitis Suppurativa severity diagnostic module 115 can segment the primary lesion 120 and any of the secondary lesions 122.

The Hidradenitis Suppurativa severity diagnostic module 115 can classify individual ones of the primary lesion 120 and any of the secondary lesions 122 into different types (papule, nodule, abscess, drainage, fistula, scar, etc.), separate colliding lesions of different types (e.g. separate a fistula from a colliding abscess). Calculate the local severity of each of the primary lesion 120 and any of the secondary lesions 122 lesion. The Hidradenitis Suppurativa severity diagnostic module 115 can measure the extensivity (diameter and surface area) of each lesion as well as of the local HS severity score 116 in an anatomical body part.

The compute system 100 can aggregate all of the local HS severity score 116 into the full body HS severity score 118 via a mathematical formula. The compute system 100, the Hidradenitis Suppurativa severity diagnostic module 115, or a combination thereof is developed, for example, using deep learning and based on a database of HS images with detailed annotations that have been done/verified by the dermatologists with the help of a team of data annotators.

Referring now to FIG. 2, therein is shown an example of a control flow of the compute system 100 with the Hidradenitis Suppurativa (HS) severity diagnostic mechanism 201 in an embodiment. The Hidradenitis Suppurativa (HS) severity diagnostic mechanism 201 accepts the patient images 114 by an OOPS detection module 202. The OOPS detection module 202 is a hardware structure executing specialized software configured to detect the presence of a skin region having a ratio greater than a non-skin region in the patient images 114. If a sufficient ratio of skin is present in the patient image 114, the flow proceeds to an image quality check module 204 to eliminate any blurry, bad luminosity, or too distant images. The image quality check module 204 can be a hardware structure executing specific software configured to verify the quality of the patient images 114. If the patient images 114 has too little skin or demonstrates poor quality (blurry, bad luminosity, or too noisy), the patient images 114 are rejected and flagged for resubmission. The image quality check module 204 can identify the acceptable image 205 for further processing.

The flow can continue to a body part detection module 206, where the acceptable image 205 is processed to detect which body part of the patient image 114 (to determine the sites such as axilla, genital, etc.). The body part detection module 206 is a hardware structure executing specialized software that is configured to detect body parts 207 reflected in the acceptable image 205. The body parts 207 can include armpits, groin, buttock, genital area, anal area, chest area, trunk, mons pubis, and sub-mammary.

In this example, the flow can continue from the body part detection module 206 to a skin segmentation module 208 and a rescale factor estimation module 210 to determine a skin region 209 and compute a rescale factor 211. In this example, the rescale factor 211 is understood as a relative number (not an absolute number) standing for the size of the patient image 114 region compared to the full body region, and from that the compute system 100, the Hidradenitis Suppurativa severity diagnostic module 115, or a combination thereof can compute the relative area of each affected region as well. The relative number can be understood as the following example: if two same size lesions are found on a baby and an adult, then the lesion on the baby should be considered as a bigger relative area since the baby body surface is much smaller than the adult's.

In this example, using skin segmentation module 208, the non-skin regions are blacked-out by a normalization module 212 to reduce noise (from non-skin region) for next steps. The normalization module 212 can format the acceptable image 205. Using the rescale factor 211, the compute system 100, the HS severity diagnostic module 115, or a combination thereof can normalize the acceptable image 205 to get a normalized image 213, such as a 512×512×3 pixel image.

In this example, the compute system 100, the Hidradenitis Suppurativa severity diagnostic module 115, or a combination thereof can operate a HS affected area segmentation module 216 to segment HS affected areas 217 (including all regions affected by HS and erythema).

Based on HS affected area 217, the flow can continue to separate each separate disconnected affected region to crop them into many smaller cropped images 219, each of the cropped images 219 corresponding to the HS affected area 217, an HS separation and cropping module 218 can crop in a way that makes the HS affected area 217 stay in the center of the cropped image 219.

The flow can continue to a HS classification module 220 to identify types of each cropped image 219 using the HS classification module 220. The HS classification module 220 is a hardware structure executing software as a regression model that does not only classify HS lesions 215 into sub-type, but also calculates a granular local severity score (which is a fractional number instead of a whole number) for each of the HS lesions 215.

The flow can continue to also put the normalized image 213 to a HS multi-label segmentation module 214 to segment the normalized image 213 into several different regions standing for different types of the HS lesion 215 (nodule, abscess, fistula, scar, drainage, papule). A compute relative area and local HS severity score module 222 is used to correlate the results of the HS multi-label segmentation module 214 and the HS classification module 220. The compute relative area and local HS severity score module 222 is a hardware structure executing software to identify the HS lesion 215 as type and sub-type as well as calculating a local HS severity score 223 for each of the HS lesions 215 identified on one of the body parts 207 in the patient image 114.

Continuing this example, the flow can continue to a display HS severity score module 224 that lists each of the HS lesions 215 and the related local HS severity score 223 identified in the patient images 114. The display HS severity score module 224 is a hardware structure that allows the listing of each of the HS lesions 215 identified with its corresponding local HS severity score 223 for display to the user 112 of FIG. 1.

It has been discovered that the compute system 100 with the Hidradenitis Suppurativa (HS) severity diagnostic mechanism 201 can process the patient images 114 to identify the acceptable image 205 for processing. The acceptable image 205 can be processed to identify the HS lesions 215 and the local HS severity score 223 for display to the user 112. The normalization image 213 provides a standardized input ratio for each of the HS lesions 215 identified. This allows the standardization of the local severity scoring 223 across the patient images 114.

Figure 3:
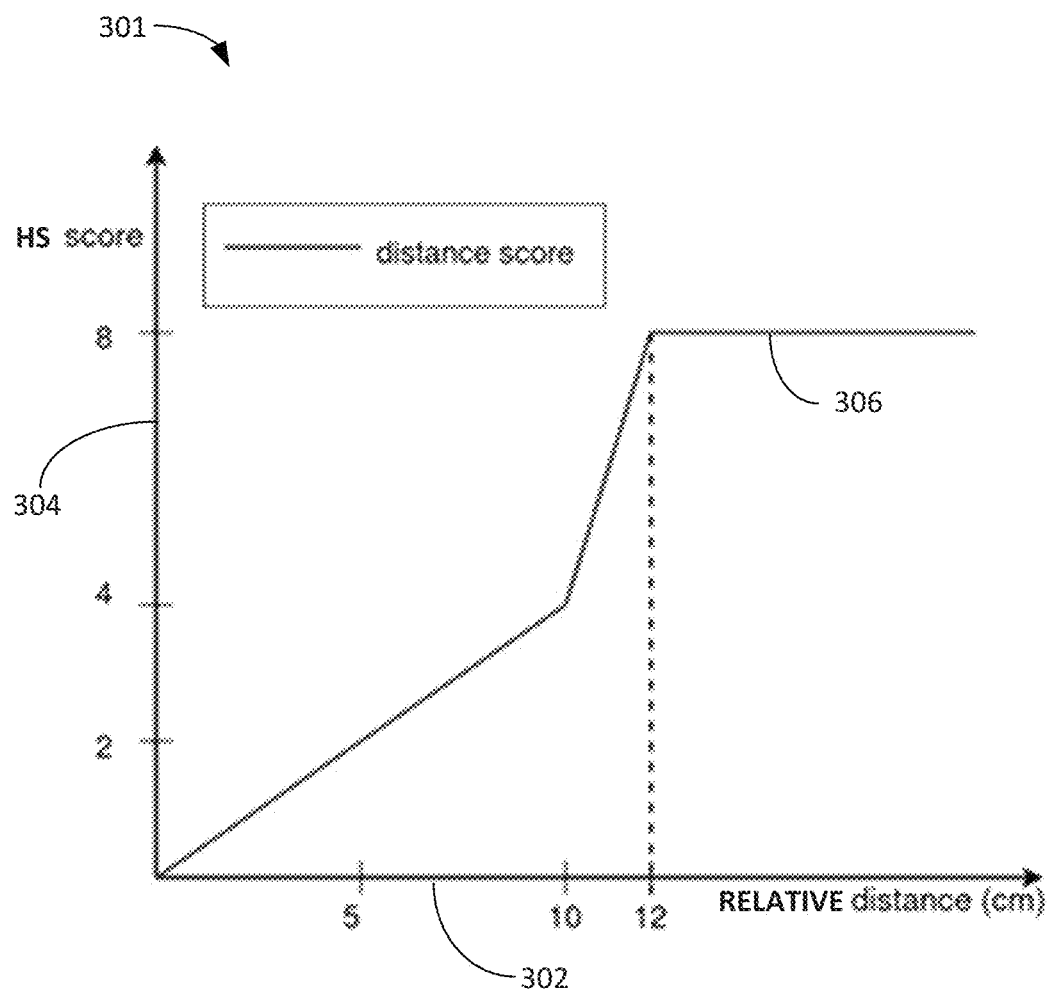
FIG. 3 is an example of a graphical representation of the process for the HS distance Score in an embodiment.

Referring now to FIG. 3, therein is shown an example of a graphical representation of the process for the HS Score 301 in an embodiment. The HS score 301 can be calculated using the body part detection module 206 of FIG. 2 and the HS affected area segmentation module 216 of FIG. 2 to determine which body part sites are involved. The process can measure the longest relative distance 302 between the primary HS lesion 120 of FIG. 1 and the secondary HS lesion 122 of FIG. 1. The relative distance 302 calculation can utilize information from the rescale factor estimation module 210 of FIG. 2 and the multi-label segmentation module 214. The HS severity AI 117 of FIG. 1 can perform the calculation of the relative distance 302.

By way of an example, an embodiment can measure density of the HS lesion 215 of FIG. 2 inside the convex hull of all HS lesions 215, as determined by the HS severity AI 117 to calculate the HS score 304. In this embodiment example, the rule is follow: if p is the proportion of lesion surface over the convex hull, then add p/100*6 points to determine a distance score 306. Continuing the example, an embodiment can add the score for each different type of the HS lesion 215 relative to the size of all types.

Figure 4:
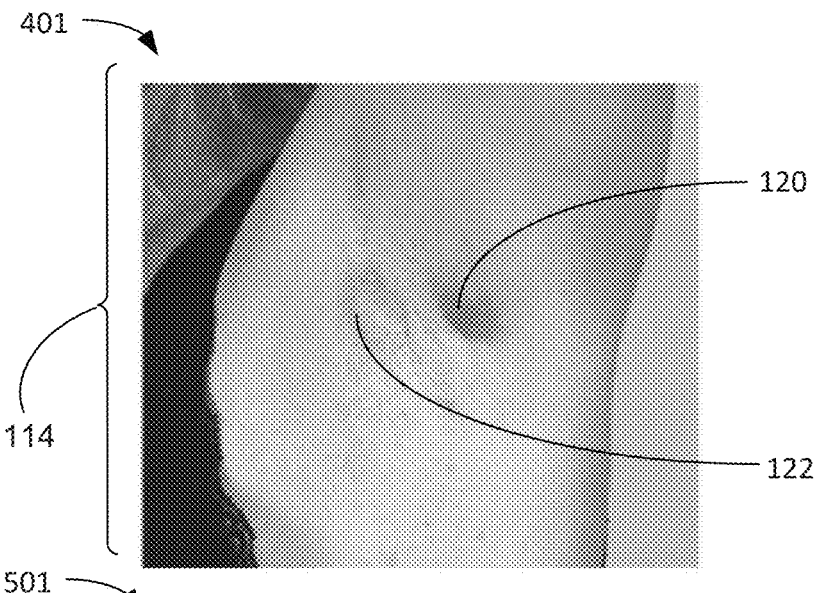
FIG. 4 is an exemplary patient image of a mild case of the Hidradenitis Suppurativa skin disease.

Referring now to FIG. 4, therein is shown an exemplary patient image 114 of a mild case 401 of the Hidradenitis Suppurativa skin disease. The patient image 114 depicts the primary HS lesion 120 as an abscess and the secondary HS lesion 122 as a nodule without sinus tracts and scarring. This can represent an early stage of the Hidradenitis Suppurativa skin disease. The HS severity AI 117 of FIG. 1 can calculate the local HS severity score 223 of FIG. 2 based on the patient image 114.

Figure 5:
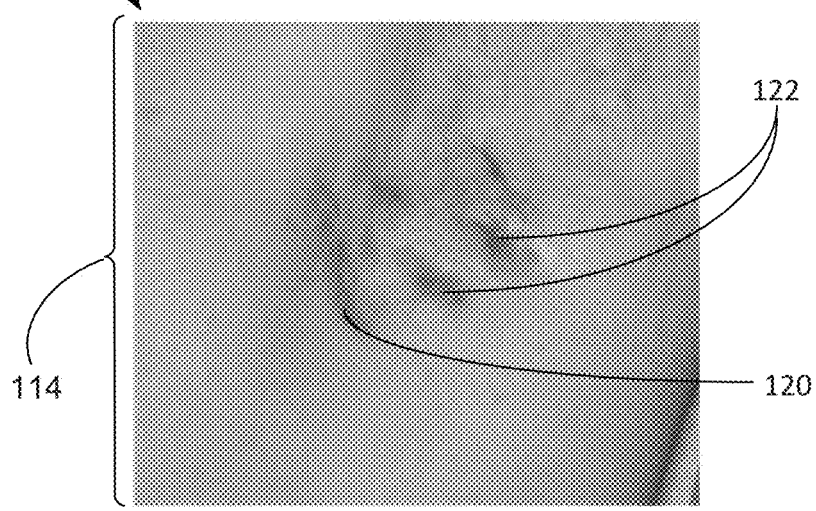
FIG. 5 is an exemplary patient image of a moderate case of the Hidradenitis Suppurativa skin disease.

Referring now to FIG. 5, therein is shown an exemplary patient image 114 of a moderate case 501 of the Hidradenitis Suppurativa skin disease. The patient image 114 depicts the primary HS lesion 120 as a single larger abscess and the multiple secondary HS lesions 122 as recurrent widely separated abscesses and nodules with sinus tract formation or scaring. This can represent an intermediate stage of the Hidradenitis Suppurativa skin disease. The HS severity AI 117 can calculate the local HS severity score 223 based on the patient image 114.

Figure 6:
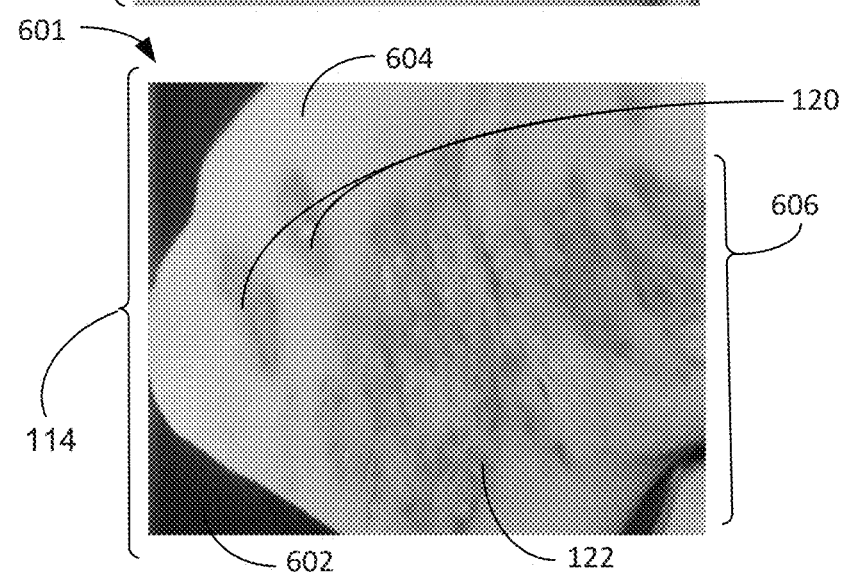
FIG. 6 is an exemplary patient image of a severe case of the Hidradenitis Suppurativa skin disease.

Referring now to FIG. 6, therein is shown an exemplary patient image 114 of a severe case 601 of the Hidradenitis Suppurativa skin disease. The patient image 114 depicts a non-skin region 602 that is blacked-out and a skin region 604 depicting the multiple of the primary HS lesion 120 as larger abscesses and a diffuse region 606 of the secondary HS lesions 122 as multiple interconnected sinus tracts, scaring, and abscesses across the entire area. This can represent an advanced stage of the Hidradenitis Suppurativa skin disease. The HS severity AI 117 can calculate the local HS severity score 223 of FIG. 2 for each of the HS lesions 215 of FIG. 2 based on the patient image 114.

Figure 7:
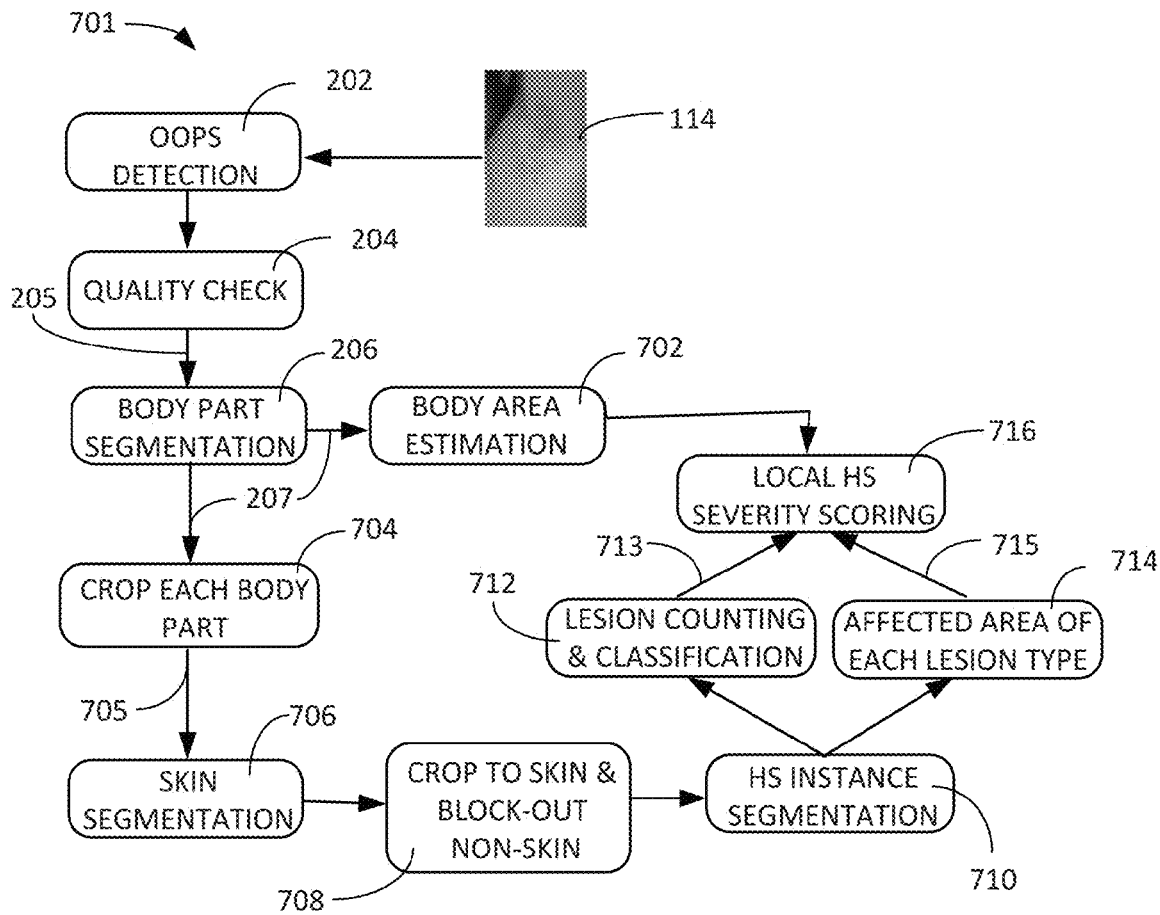
FIG. 7 is an example of a control flow of a local HS severity scoring 0 of the Hidradenitis Suppurativa severity diagnostic mechanism in an embodiment.

Referring now to FIG. 7, therein is shown an example of a control flow of a local HS severity scoring of the Hidradenitis Suppurativa severity diagnostic mechanism 701 in an embodiment. The Hidradenitis Suppurativa severity diagnostic mechanism 701 can be implemented in software running on dedicated hardware, a hardware implementation, or a combination thereof. The Hidradenitis Suppurativa severity diagnostic mechanism 701 depicts the patient image 114 submitted to the OOPS detection module 202 for verification that the patient image 114 contains sufficient skin to be processed.

The flow proceeds to the image quality check module 204 to verify that the patient image 114 is of sufficient quality (clarity, brightness, distance, and noise) to be processed by the Hidradenitis Suppurativa severity diagnostic mechanism 701. If the patient images 114 has too little skin or demonstrates poor quality (blurry, too light, too dark, or too noisy), the patient images 114 are rejected and flagged for resubmission. The image quality check module 204 can identify the acceptable image 205 for further processing.

The flow can proceed to the body part detection module 206 for identification of the body parts 207 represented by the acceptable image 205. The acceptable image 205 can be transferred to a body area estimation module 702 and a crop each body part module 704. The body area estimation module 702 is a hardware structure executing software that interfaces with the HS severity AI 117 of FIG. 1. The body area estimation module 702 can calculate the area of the body part 207 identified in the acceptable image 205. The crop each body part module 704 is a hardware structure executing software to crop the acceptable image 205 in order to center any of the body parts 207 shown in a cropped image 705.

The cropped image 705 can be processed by a skin segmentation module 706 to identify the skin region 209 of FIG. 2. The skin segmentation module 706 is a hardware structure executing software to identify the skin region 209 for further processing. A crop to skin & black-out non-skin module 708 can isolate the skin region 209 by blacking-out any non-skin areas of the cropped image 705. The crop to skin & black-out non-skin module 708 is a hardware structure executing software in order to enhance the identification of the skin region 209.

The flow proceeds to a HS instance segmentation module 710 for identification of areas that include the HS lesions 215 of FIG. 2. The HS instance segmentation module 710 is a hardware structure executing software to interface with the HS severity AI 117 to identify the HS lesions 215 present in the body parts 207 captured in the cropped image 705. The HS instance segmentation module 710 can be coupled to a lesion counting & classification module 712 and an affected area of each lesion type module 714. The HS lesion counting & classification module 712 is a hardware structure executing software to identify the types of the HS lesions 215 and count each of the different types of the HS lesions 215. The HS lesion counting & classification module 712 can generate an accounting of HS lesions 713 listing the number and type of the HS lesions 215 identified. The affected area of each lesion type module 714 is a hardware structure executing software to calculate an affected area 715 for each of the types of the HS lesions 215 identified by the HS instance segmentation module 710.

A local HS severity scoring module 716 is a hardware structure executing software in order to assign the local HS severity score 223 of FIG. 2 for each of the HS lesions 215 that have been identified in one of the body parts 207 of the cropped image 705. The local HS severity scoring module 716 can generate the local HS severity score 223 for a single body part 207. The local HS severity scoring module 716 can process the accounting of lesions 713 and the affected area 715 for each of the HS lesions 215 identified in the cropped image 705. The local HS severity scoring module 716 can represent a portion of the HS severity AI 117 in analyzing the local HS severity score 223 for each of the body parts 207 analyzed by the Hidradenitis Suppurativa severity diagnostic mechanism 701.

Figure 8:
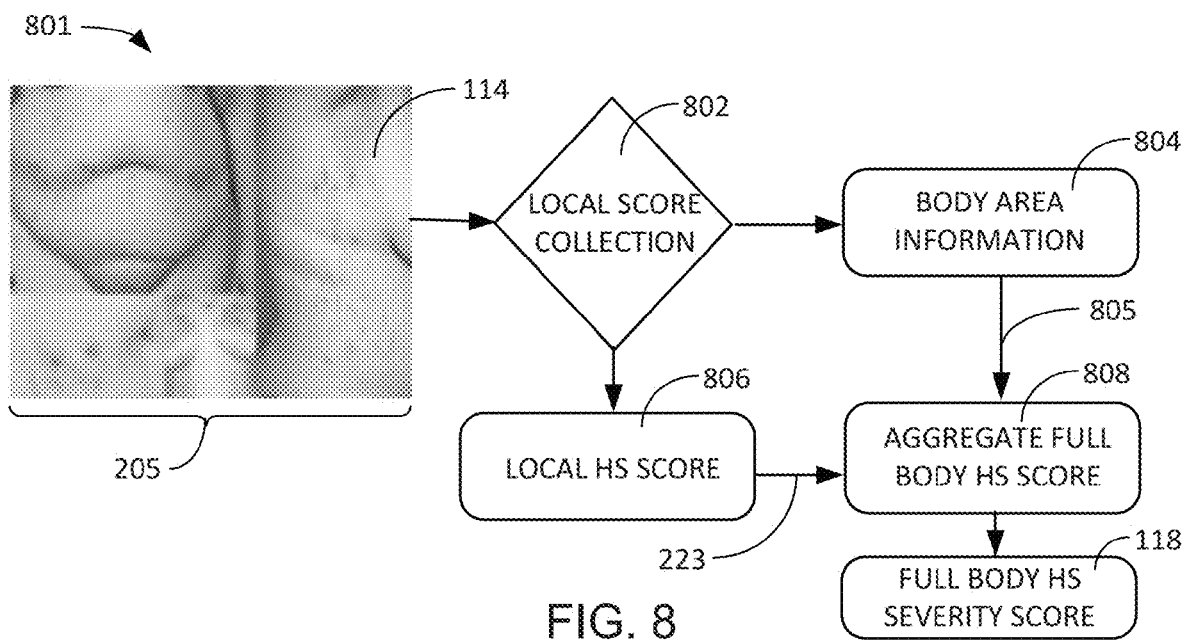
FIG. 8 is an example of a control flow of an aggregation mechanism for the full body HS severity score.

Referring now to FIG. 8, therein is shown an example of a control flow of an aggregation mechanism 801 for the full body HS severity score 118 of FIG. 1. The aggregation mechanism 801 is a hardware structure executing software to identify the local HS severity score 223 of FIG. 2 for each of the patient images 114 representing the body parts 205. The aggregation mechanism 801 can include a local score collection module 802 that aggregates the local HS severity score 223 from each of the body parts 205 that display the HS lesions 215 of FIG. 2, as collected by the Hidradenitis Suppurativa severity diagnostic mechanism 701 of FIG. 7.

The local score collection module 802 can be coupled to a body area information module 804 and a local HS score module 806. The body area information module 804 is a hardware structure executing software configured to collect the affected area 715 of FIG. 7 for each of the body parts 205. The local HS score module 806 is a hardware structure executing software configured to present the local HS severity score 223 from each of the HS lesions 215 detected by the local score collection module 802 to generate a body part area 805.

An aggregate full body HS score module 808 is a hardware structure executing software configured to aggregate the local HS severity score 223 and the affected area 715 of FIG. 7 presented as the body part area 805. The aggregate full body HS score module 808 can support the calculation of the full body HS severity score 118.

Figure 9:
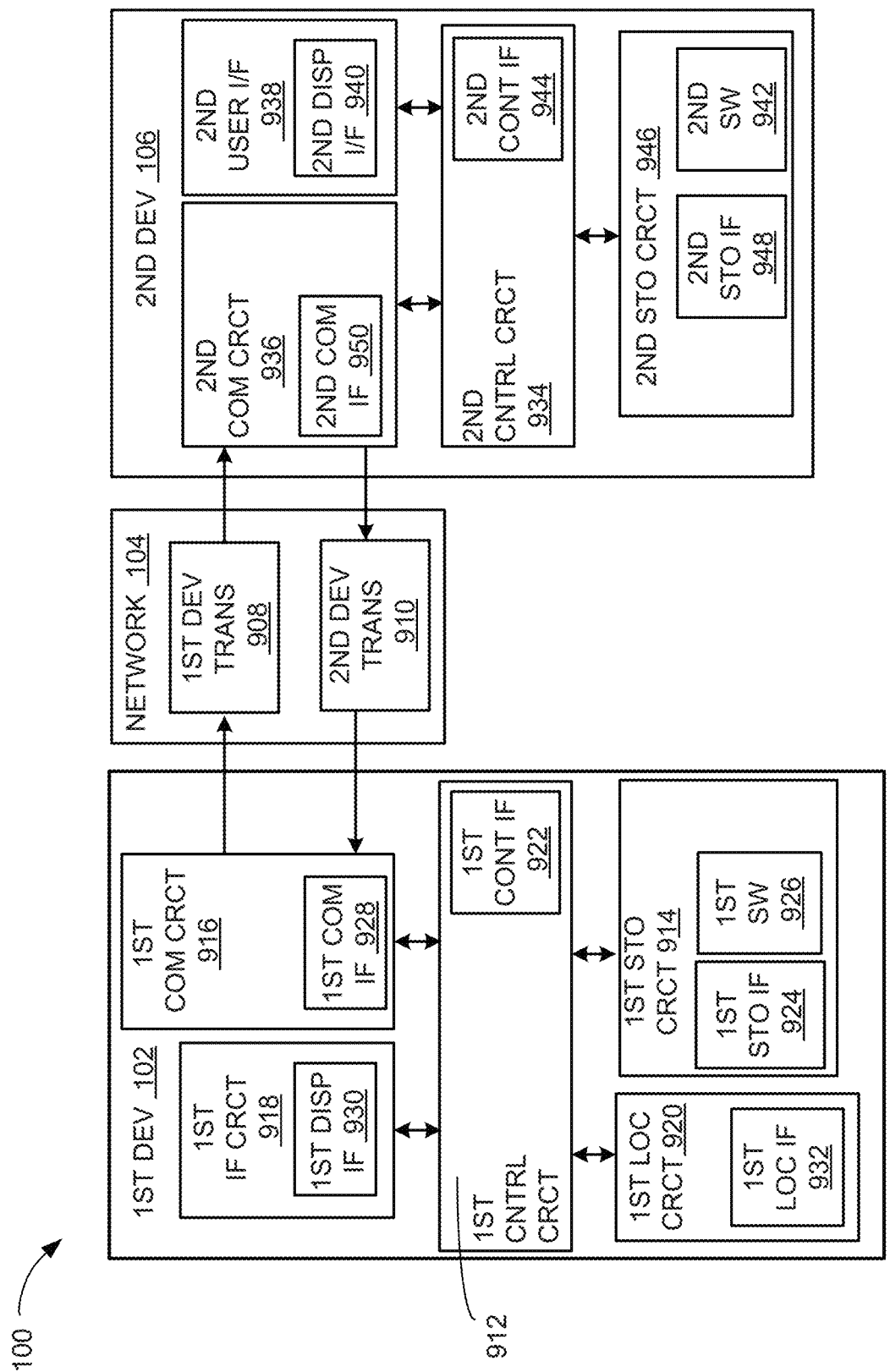
FIG. 9 is an exemplary block diagram of the compute system in an embodiment.

Referring now to FIG. 9, therein is shown an exemplary block diagram of the compute system 100 in an embodiment. The compute system 100 can include the first device 102, the network 104, and the second device 106. The first device 102 can send information in a first device transmission 908 over the network 104 to the second device 106. The second device 106 can send information in a second device transmission 910 over the network 104 to the first device 102.

For illustrative purposes, the compute system 100 is shown with the first device 102 as a client device, although it is understood that the compute system 100 can include the first device 102 as a different type of device, such as a vehicle, a smart phone, a camera, or other monitoring device.

Also, for illustrative purposes, the compute system 100 is shown with the second device 106 as a server, although it is understood that the compute system 100 can include the second device 106 as a different type of device. For example, the second device 106 can be a client device. By way of an example, the compute system 100 can be implemented entirely on the first device 102.

Also, for illustrative purposes, the compute system 100 is shown with interaction between the first device 102 and the second device 106. However, it is understood that the first device 102 can be a vehicle, a smart phone, a camera, or a combination thereof. Similarly, the second device 106 can similarly interact with the first device 102 representing the vehicle, the smart phone, the camera, or a combination thereof.

For brevity of description in this embodiment of the present invention, the first device 102 will be described as a client device or the smart phone, and the second device 106 will be described as a server device. The embodiment of the present invention is not limited to this selection for the type of devices. The selection is an example of an embodiment of the present invention.

The first device 102 can include a first control circuit 912, a first storage circuit 914, a first communication circuit 916, a first interface circuit 918, and a first location circuit 920. The first control circuit 912 can include a first control interface 922. The first control circuit 912 can execute a first software 926 to provide the intelligence of the compute system 100.

The first control circuit 912 can be implemented in a number of different manners. For example, the first control circuit 912 can be a processor, an application specific integrated circuit (ASIC) an embedded processor, a microprocessor, a hardware control logic, a hardware finite state machine (FSM), a digital signal processor (DSP), or a combination thereof. The first control interface 922 can be used for communication between the first control circuit 912 and other functional units or circuits in the first device 102. The first control interface 922 can also be used for communication that is external to the first device 102.

The first control interface 922 can receive information from the other functional units/circuits or from external sources, or can transmit information to the other functional units/circuits or to external destinations. The external sources and the external destinations refer to sources and destinations external to the first device 102.

The first control interface 922 can be implemented in different ways and can include different implementations depending on which functional units/circuits or external units/circuits are being interfaced with the first control interface 922. For example, the first control interface 922 can be implemented with a pressure sensor, an inertial sensor, a microelectromechanical system (MEMS), optical circuitry, waveguides, wireless circuitry, wireline circuitry, or a combination thereof.

The first storage circuit 914 can store the first software 926. The first storage circuit 914 can also store the relevant information, such as data representing patient images 114 of FIG. 1, data representing the body parts 207 of FIG. 2, sound files, or a combination thereof.

The first storage circuit 914 can be a volatile memory, a nonvolatile memory, an internal memory, an external memory, or a combination thereof. For example, the first storage circuit 914 can be a nonvolatile storage such as non-volatile random-access memory (NVRAM), Flash memory, disk storage, or a volatile storage such as static random-access memory (SRAM).

The first storage circuit 914 can include a first storage interface 924. The first storage interface 924 can be used for communication between the first storage circuit 914 and other functional units or circuits in the first device 102. The first storage interface 924 can also be used for communication that is external to the first device 102.

The first storage interface 924 can receive information from the other functional units/circuits or from external sources, or can transmit information to the other functional units/circuits or to external destinations. The external sources and the external destinations refer to sources and destinations external to the first device 102. The first storage interface 924 can receive input from and source data to the Hidradenitis Suppurativa severity diagnostic module 115 of FIG. 1.

The first storage interface 924 can include different implementations depending on which functional units/circuits or external units/circuits are being interfaced with the first storage circuit 914. The first storage interface 924 can be implemented with technologies and techniques similar to the implementation of the first control interface 922.

The first communication circuit 916 can enable external communication to and from the first device 102. For example, the first communication circuit 916 can permit the first device 102 to communicate with the second device 106 and the network 104.

The first communication circuit 916 can also function as a communication hub allowing the first device 102 to function as part of the network 104 and not limited to be an endpoint or terminal circuit to the network 104. The first communication circuit 916 can include active and passive components, such as microelectronics or an antenna, for interaction with the network 104.

The first communication circuit 916 can include a first communication interface 928. The first communication interface 928 can be used for communication between the first communication circuit 916 and other functional units or circuits in the first device 102. The first communication interface 928 can receive information from the second device 106 for distribution to the other functional units/circuits or can transmit information to the other functional units or circuits.

The first communication interface 928 can include different implementations depending on which functional units or circuits are being interfaced with the first communication circuit 916. The first communication interface 928 can be implemented with technologies and techniques similar to the implementation of the first control interface 922.

The first interface circuit 918 allows the user 112 of FIG. 1 to interface and interact with the first device 102. The first interface circuit 918 can include an input device and an output device. Examples of the input device of the first interface circuit 918 can include a keypad, a touchpad, soft-keys, a keyboard, a microphone, an infrared sensor for receiving remote signals, or any combination thereof to provide data and communication inputs.

The first interface circuit 918 can include a first display interface 930. The first display interface 930 can include an output device capable of presenting the full body HS severity score 118 of FIG. 1. The first display interface 930 can include a projector, a video screen, a touch screen, a speaker, a microphone, a keyboard, and combinations thereof.

The first control circuit 912 can operate the first interface circuit 918 to display information generated by the compute system 100 and receive input from the user 112. The first control circuit 912 can also execute the first software 926 for the other functions of the compute system 100, including receiving location information from the first location circuit 920. The first control circuit 912 can further execute the first software 926 for interaction with the network 104 via the first communication circuit 916. The first control circuit 912 can operate the Hidradenitis Suppurativa diagnostic mechanism 115.

The first control circuit 912 can also receive location information from the first location circuit 920. The first control circuit 912 can operate the Hidradenitis Suppurativa severity diagnostic module 115 including the HS severity AI 117 of FIG. 1.

The first location circuit 920 can be implemented in many ways. For example, the first location circuit 920 can function as at least a part of the global positioning system, an inertial compute system, a cellular-tower location system, a gyroscope, or any combination thereof. Also, for example, the first location circuit 920 can utilize components such as an accelerometer, gyroscope, or global positioning system (GPS) receiver.

The first location circuit 920 can include a first location interface 932. The first location interface 932 can be used for communication between the first location circuit 920 and other functional units or circuits in the first device 102.

The first location interface 932 can receive information from the other functional units/circuits or from external sources, or can transmit information to the other functional units/circuits or to external destinations. The external sources and the external destinations refer to sources and destinations external to the first device 102. The first location interface 932 can receive the global positioning location from the global positioning system (not shown).

The first location interface 932 can include different implementations depending on which functional units/circuits or external units/circuits are being interfaced with the first location circuit 920. The first location interface 932 can be implemented with technologies and techniques similar to the implementation of the first control circuit 912.

The second device 106 can be optimized for implementing an embodiment of the present invention in a multiple device embodiment with the first device 102. The second device 106 can provide the additional or higher performance processing power compared to the first device 102. The second device 106 can include a second control circuit 934, a second communication circuit 936, a second user interface 938, and a second storage circuit 946.

The second user interface 938 allows an operator (not shown) to interface and interact with the second device 106. The second user interface 938 can include an input device and an output device. Examples of the input device of the second user interface 938 can include a keypad, a touchpad, soft-keys, a keyboard, a microphone, or any combination thereof to provide data and communication inputs. Examples of the output device of the second user interface 938 can include a second display interface 940. The second display interface 940 can include a display, a projector, a video screen, a speaker, or any combination thereof.

The second control circuit 934 can execute a second software 942 to provide the intelligence of the second device 106 of the compute system 100. The second software 942 can operate in conjunction with the first software 926. The second control circuit 934 can provide additional performance compared to the first control circuit 912.

The second control circuit 934 can operate the second user interface 938 to display information. The second control circuit 934 can also execute the second software 942 for the other functions of the compute system 100, including operating the second communication circuit 936 to communicate with the first device 102 over the network 104. The second control circuit 934 can operate the Hidradenitis Suppurativa severity diagnostic module 115 including the HS severity AI 117 of FIG. 1.

The second control circuit 934 can be implemented in a number of different manners. For example, the second control circuit 934 can be a processor, an embedded processor, a microprocessor, hardware control logic, a hardware finite state machine (FSM), a digital signal processor (DSP), or a combination thereof.

The second control circuit 934 can include a second control interface 944. The second control interface 944 can be used for communication between the second control circuit 934 and other functional units or circuits in the second device 106. The second control interface 944 can also be used for communication that is external to the second device 106.

The second control interface 944 can receive information from the other functional units/circuits or from external sources, or can transmit information to the other functional units/circuits or to external destinations. The external sources and the external destinations refer to sources and destinations external to the second device 106.

The second control interface 944 can be implemented in different ways and can include different implementations depending on which functional units/circuits or external units/circuits are being interfaced with the second control interface 944. For example, the second control interface 944 can be implemented with a pressure sensor, an inertial sensor, a microelectromechanical system (MEMS), optical circuitry, waveguides, wireless circuitry, wireline circuitry, or a combination thereof.

The second storage circuit 946 can store the second software 942. The second storage circuit 946 can also store the information such as data representing incoming images, data representing previously presented image, sound files, or a combination thereof. The second storage circuit 946 can be sized to provide the additional storage capacity to supplement the first storage circuit 914.

For illustrative purposes, the second storage circuit 946 is shown as a single element, although it is understood that the second storage circuit 946 can be a distribution of storage elements. Also, for illustrative purposes, the compute system 100 is shown with the second storage circuit 946 as a single hierarchy storage system, although it is understood that the compute system 100 can include the second storage circuit 946 in a different configuration. For example, the second storage circuit 946 can be formed with different storage technologies forming a memory hierarchal system including different levels of caching, main memory, rotating media, or off-line storage.

The second storage circuit 946 can be a controller of a volatile memory, a nonvolatile memory, an internal memory, an external memory, or a combination thereof. For example, the second storage circuit 946 can be a controller of a nonvolatile storage such as non-volatile random-access memory (NVRAM), Flash memory, disk storage, or a volatile storage such as static random access memory (SRAM).

The second storage interface 948 can receive information from the other functional units/circuits or from external sources, or can transmit information to the other functional units/circuits or to external destinations. The external sources and the external destinations refer to sources and destinations external to the second device 106.

The second storage interface 948 can include different implementations depending on which functional units/circuits or external units/circuits are being interfaced with the second storage circuit 946. The second storage interface 948 can be implemented with technologies and techniques similar to the implementation of the second control interface 944.

The second communication circuit 936 can enable external communication to and from the second device 106. For example, the second communication circuit 936 can permit the second device 106 to communicate with the first device 102 over the network 104.

The second communication circuit 936 can also function as a communication hub allowing the second device 106 to function as part of the network 104 and not limited to be an endpoint or terminal unit or circuit to the network 104. The second communication circuit 936 can include active and passive components, such as microelectronics or an antenna, for interaction with the network 104.

The second communication circuit 936 can include a second communication interface 950. The second communication interface 950 can be used for communication between the second communication circuit 936 and other functional units or circuits in the second device 106. The second communication interface 950 can receive information from the other functional units/circuits or can transmit information to the other functional units or circuits.

The second communication interface 950 can include different implementations depending on which functional units or circuits are being interfaced with the second communication circuit 936. The second communication interface 950 can be implemented with technologies and techniques similar to the implementation of the second control interface 944.

The second communication circuit 936 can couple with the network 104 to send information to the first device 102. The first device 102 can receive information in the first communication circuit 916 from the second device transmission 910 of the network 104. The compute system 100 can be executed by the first control circuit 912, the second control circuit 934, or a combination thereof. For illustrative purposes, the second device 106 is shown with the partition containing the second user interface 938, the second storage circuit 946, the second control circuit 934, and the second communication circuit 936, although it is understood that the second device 106 can include a different partition. For example, the second software 942 can be partitioned differently such that some or all of its function can be in the second control circuit 934 and the second communication circuit 936. Also, the second device 106 can include other functional units or circuits not shown in FIG. 9 for clarity.

The functional units or circuits in the first device 102 can work individually and independently of the other functional units or circuits. The first device 102 can work individually and independently from the second device 106 and the network 104.

The functional units or circuits in the second device 106 can work individually and independently of the other functional units or circuits. The second device 106 can work individually and independently from the first device 102 and the network 104.

The functional units or circuits described above can be implemented in hardware. For example, one or more of the functional units or circuits can be implemented using a gate array, an application specific integrated circuit (ASIC), circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

For illustrative purposes, the compute system 100 is described by operation of the first device 102 and the second device 106. It is understood that the first device 102 and the second device 106 can operate any of the modules and functions of the compute system 100.

Figure 10:
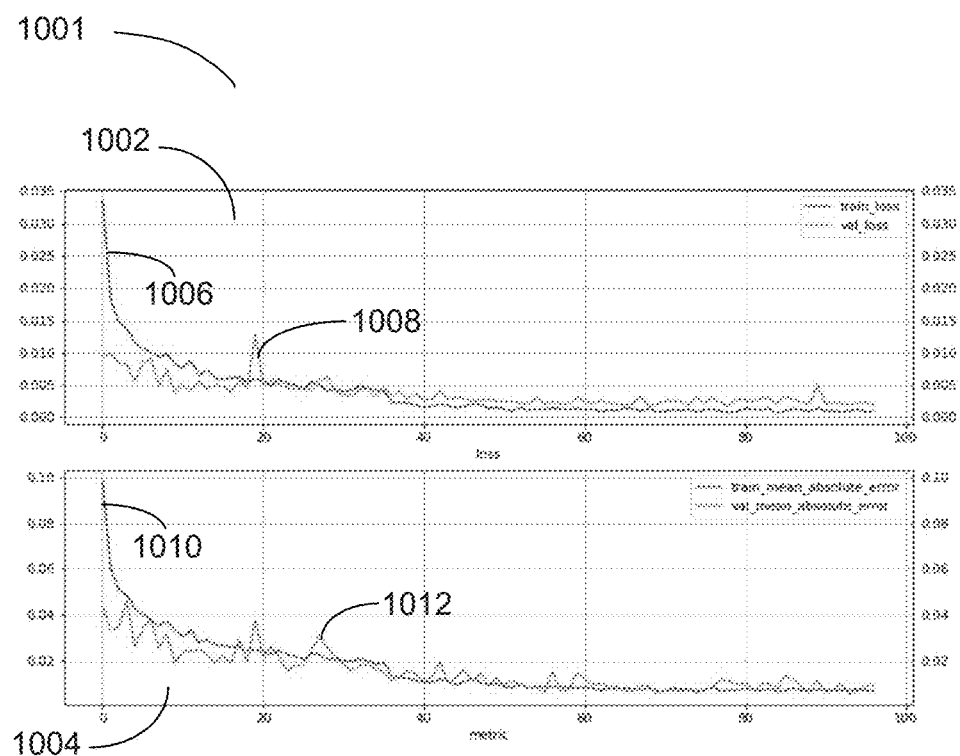
FIG. 10 is an example of the performance chart of the oops detection module of FIG. 2 in an embodiment.

Referring now to FIG. 10, therein is shown an example of the performance chart 1001 of the oops detection module 202 of FIG. 2 in an embodiment. The compute system 100, the Hidradenitis Suppurativa severity diagnostic module 115, of FIG. 1 or a combination thereof can be trained for 95 epochs with nearly 40000 images in each epoch, about 80% data set is reserved for training set and the rest for validation. To measure the accuracy of the model, MAE as equation 3.1 can be utilized.

As an example, the performance from training for the compute system 100, the Hidradenitis Suppurativa severity diagnostic module 115, or a combination thereof can be shown with a loss chart 1002 and an absolute error chart 1004. Continuing with the example, the loss chart 1002 depicts the performance to handle the data imbalance issue in learning deep regression networks. For this task, the compute system 100, the Hidradenitis Suppurativa severity diagnostic module 115, or a combination thereof can use Shrinkage loss function, which is defined as below:

$$l(y, \hat{y}) = \frac{m^2}{1 + \exp[a.(c - m)]}$$

where $m=|y-\hat{y}|$, y is the true label and $\hat{y}$ is the prediction, a and c are hyper-parameters controlling the Shrinkage speed and the localization respectively.

Regarding the loss and metric, the metric to measure accuracy of the model is mean absolute error (MAE) that is a measure of errors between paired observations expressing the same phenomenon. MAE is calculated as the sum of absolute errors divided by the sample size:

$$MAE = \frac{1}{n}\sum_{j=1}^{n}|y_j - \hat{y}_j| \quad (3.1)$$

where $y_j$ are the true labels and $\hat{y}_j$ are the corresponding predictions.

The compute system 100, can aggregate all of the local HS severity score 116 into the full body HS severity score 118 to obtain 0.01 MAE score on validation. FIG. 10 illustrates for the performance of Oops detection module 202.

A loss chart 1002 indicates the loss function of a training loss 1006 as compared to a verification loss 1008 based on the number of epochs used to train the HS severity diagnostic module 115. As displayed in the loss chart 1002, the verification loss 1008 tracks the training loss 1006 with 0.002 after 95 epochs of training.

An absolute error chart 1004 indicates the mean absolute error of a training error 1010 as compared to a verification error 1012 based on the number of epochs used to train the skin disease identification module 116. As displayed in the absolute error chart 1004, the verification error 1012 tracks the training error 1010 with 0.1 mean absolute error between the predicted values and the absolute values after 95 epochs of training.

Figure 11:
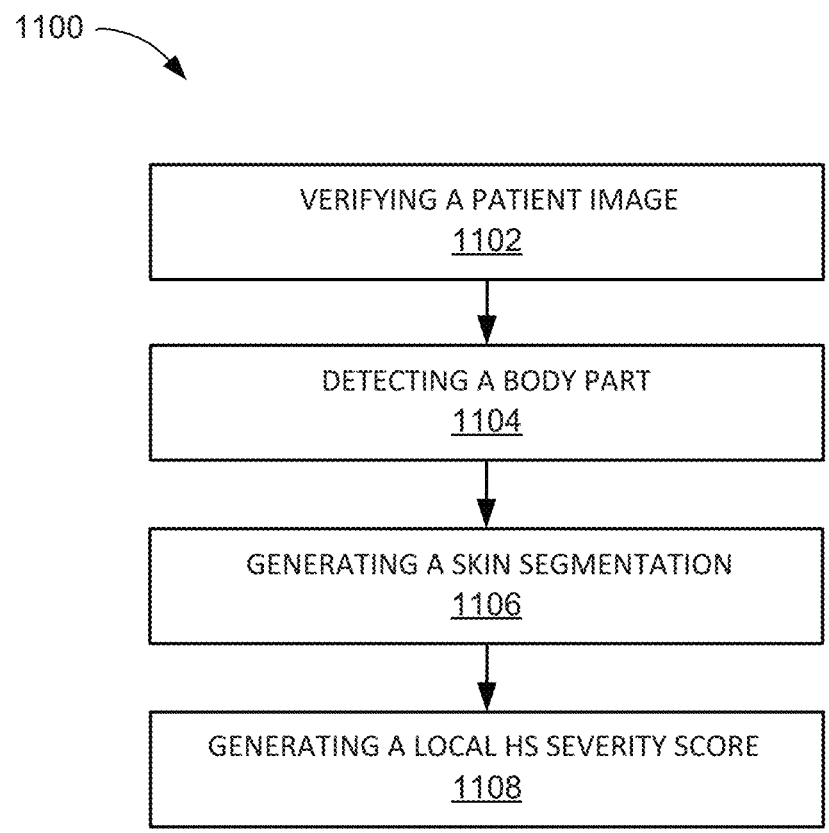
FIG. 11 is a flow chart of a method of operation of a compute system in an embodiment of the present invention.

Referring now to FIG. 11, therein is shown a flow chart of a method 1100 of operation of a compute system 100 of FIG. 1 in an embodiment of the present invention. The method 1100 includes: verifying a patient image as an acceptable image in a block 1102; detecting a body part from the acceptable image in a block 1104; generating a skin segmentation for the body part including a non-skin region and a skin region based on the acceptable image in a block 1106; and generating a local Hidradenitis Suppurativa (HS) severity score based on the patient image for displaying on a device to assist in diagnosis in a block 1108.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of operation of a compute system comprising:
   verifying a patient image as an acceptable image;
   detecting a body part from the acceptable image;
   generating a skin segmentation for the body part including a non-skin region and a skin region based on the acceptable image;

generating a normalized image with a rescale factor based on the skin segmentation and the patient image;

identifying a type of an Hidradenitis Suppurativa (HS) lesion from among a nodule, an abscess, a fistula, a scar drainage, and a papule based on the normalized image; and generating a local HS severity score based on the patient type of the HS lesion for displaying on a device to assist in diagnosis.

2. The method as claimed in claim 1 further comprising generating a full body HS severity score including aggregating the local HS severity score and the body part area detected in the patient image.

3. The method as claimed in claim 1 wherein verifying the patient image includes detecting a skin region and a non-skin region to verify the skin region ratio greater than the non-skin region.

4. The method as claimed in claim 1 wherein verifying the acceptable image includes performing an image quality check to eliminate the patient image that is blurry, includes bad luminosity, or a combination thereof.

5. The method as claimed in claim 1 further comprising generating an accounting of HS lesions includes segmenting the HS instances of a cropped image and counting and classifying the HS lesions identified in the cropped image.

6. The method as claimed in claim 1 wherein generating the local HS severity score includes estimating the body area of the body part, counting and classifying the HS lesions, and calculating the affected area of the HS lesions in the cropped image.

7. The method as claimed in claim 1 wherein generating the normalized image includes cropping the acceptable image as a 512×512×3 pixel image.

8. A compute system comprising:
a control circuit, including a processor, configured to:
verify an acceptable image from a patient image,
detect a body part from the acceptable image,
generate a skin segmentation for the body part including a non-skin region and a skin region based on the acceptable image, and
generate a normalized image with a rescale factor based on the skin segmentation and the patient image;
identify a type of an Hidradenitis Suppurativa (HS) lesion from among a nodule, an abscess, a fistula, a scar, drainage, and a papule based on the normalized image; and
generate a local HS severity score based on the type of the HS lesion for displaying on a device to assist in diagnosis.

9. The compute system as claimed in claim 8, further comprising a full body HS severity score generated includes the local HS severity score and the body part area aggregated and detected in the patient image.

10. The compute system as claimed in claim 8, wherein the patient image verified includes a skin region and a non-skin region detected to verify the skin region ratio greater than the non-skin region.

11. The compute system as claimed in claim 8, wherein the acceptable image verified includes an image quality check performed to eliminate the patient image that is blurry, includes bad luminosity, or a combination thereof.

12. The compute system as claimed in claim 8, further comprising an accounting of HS lesions verified includes the HS instances of a cropped image segmented and counting and classifying the HS lesions identified in the cropped image.

13. The compute system as claimed in claim 8, wherein the local HS severity score generated includes the body area of the body part estimated, the HS lesions counted and classified, and the affected area of the HS lesions calculated in the cropped image.

14. The compute system as claimed in claim 8, wherein the normalized image generated includes the acceptable image cropped as a 512×512×3 pixel image.

15. A non-transitory computer readable medium including instructions for a compute system comprising:
verifying an acceptable image from a patient image;
detecting a body part from the acceptable image;
generating a skin segmentation for the body part including a non-skin region and a skin region based on the acceptable image;
generating a normalized image with a rescale factor based on the skin segmentation and the patient image;
identifying a type of an Hidradenitis Suppurativa (HS) lesion from among a nodule, an abscess, a fistula, a scar, drainage, and a papule based on the normalized image; and
generating a local HS severity score based on the type of the HS lesion for displaying on a device to assist in diagnosis.

16. The non-transitory computer readable medium including instructions for a compute system, as claimed in claim 15, further comprising generating a full body HS severity score including aggregating the local HS severity score and the body part area detected in the patient image.

17. The non-transitory computer readable medium including instructions for a compute system, as claimed in claim 15, wherein verifying the patient image includes detecting a skin region and a non-skin region to verify the skin region ratio greater than the non-skin region.

18. The non-transitory computer readable medium including instructions for a compute system, as claimed in claim 15, wherein verifying the acceptable image includes performing an image quality check to eliminate the patient image that is blurry, includes bad luminosity, or a combination thereof.

19. The non-transitory computer readable medium including instructions for a compute system, as claimed in claim 15, further comprising generating an accounting of HS lesions includes segmenting the HS instances of a cropped image and counting and classifying the HS lesions identified in the cropped image.

20. The non-transitory computer readable medium including instructions for a compute system, as claimed in claim 15, wherein generating the local HS severity score includes estimating the body area of the body part, counting and classifying the HS lesions, and calculating the affected area of the HS lesions in the cropped image.

* * * * *